(12) United States Patent
Nishiyama et al.

(10) Patent No.: US 8,304,216 B2
(45) Date of Patent: Nov. 6, 2012

(54) METHOD FOR PRODUCTION OF ERYTHRO-OR THREO-2-AMINO-3-HYDROXYPROPIONIC ACID ESTER, NOVEL CARBONYL REDUCTASE, GENE FOR THE REDUCTASE, VECTOR, TRANSFORMANT, AND METHOD FOR PRODUCTION OF OPTICALLY ACTIVE ALCOHOL USING THOSE

(75) Inventors: Tozo Nishiyama, Takasago (JP); Yoshihiko Yasohara, Takasago (JP)

(73) Assignee: Kaneka Corporation, Osaka (JP)

( * ) Notice: Subject to any disclaimer, the term of this patent is extended or adjusted under 35 U.S.C. 154(b) by 982 days.

(21) Appl. No.: 12/225,683

(22) PCT Filed: Mar. 29, 2007

(86) PCT No.: PCT/JP2007/056798
§ 371 (c)(1),
(2), (4) Date: Nov. 25, 2008

(87) PCT Pub. No.: WO2007/114217
PCT Pub. Date: Nov. 10, 2007

(65) Prior Publication Data
US 2009/0186391 A1    Jul. 23, 2009

(30) Foreign Application Priority Data
Mar. 31, 2006    (JP) ................................. 2006-096941

(51) Int. Cl.
*C12P 7/02* (2006.01)
*C12P 7/62* (2006.01)
*C07H 21/04* (2006.01)

(52) U.S. Cl. .................... 435/135; 435/155; 435/320.1; 536/23.1

(58) Field of Classification Search ........................ None
See application file for complete search history.

(56) References Cited

U.S. PATENT DOCUMENTS

| 7,220,564 B2 * | 5/2007 | Kizaki et al. ................. 435/189 |
| 2005/0137421 A1 * | 6/2005 | Walsh et al. ................. 562/446 |
| 2006/0035357 A1 | 2/2006 | Kizaki et al. |
| 2006/0167300 A1 | 7/2006 | Hamada et al. |

FOREIGN PATENT DOCUMENTS

| EP | 1 179 595 A1 | 2/2002 |
| EP | 1 452 588 A1 | 9/2004 |
| EP | 1 553 170 A1 | 7/2005 |
| JP | 2007-29089 A | 2/2007 |
| JP | 2007029089 A * | 2/2007 |
| WO | WO-2004/027055 A1 | 4/2004 |
| WO | WO 2005/005371 A1 | 1/2005 |

OTHER PUBLICATIONS

English machine translation for JP 2007-029089 downloaded from the JPO on Aug. 24, 2011.*
Peters et al., "A Novel NADH-dependent Carbonyl Reductase with an Extremely Broad Substrate Range From *Candida parapsilosis*: Purification and Characterization", Enzyme Microb. Technol., Nov. 1993, pp. 950-958, vol. 15, XP-001094568.
Kataoka et al., "Novel Bioreduction System for the Production of Chiral Alcohols", Appl Microbiol Bioltechnol, 2003, pp. 437-445, vol. 62, XP009049508.
International Preliminary Report on Patentability issued on Oct. 21, 2008, in connection with PCT International Application No. PCT/JP2007/056798.
M. Alonso et al., Organic Process Research & Development 2005, 9, 690-693.

* cited by examiner

*Primary Examiner* — Tekchand Saidha
*Assistant Examiner* — Md. Younus Meah
(74) *Attorney, Agent, or Firm* — Birch, Stewart, Kolasch & Birch, LLP

(57) ABSTRACT

The present invention has its object to provide a method of producing an erythro- or threo-2-amino-3-hydroxypropionic acid ester, and so forth. The present invention relates to: a method of asymmetrically reducing an N-2-amino-3-oxopropionic acid ester by allowing cells of a microorganism to act thereon; a polypeptide having an activity of asymmetrically reducing a carbonyl compound to give an optically active alcohol, which is isolated from a microorganism belonging to genus *Brevundimonas*; a DNA coding for the polypeptide; and a transformant producing the polypeptide. The invention also relates to a method of producing an optically active alcohol by reducing a carbonyl compound with the help of the polypeptide or the transformant.

1 Claim, 1 Drawing Sheet

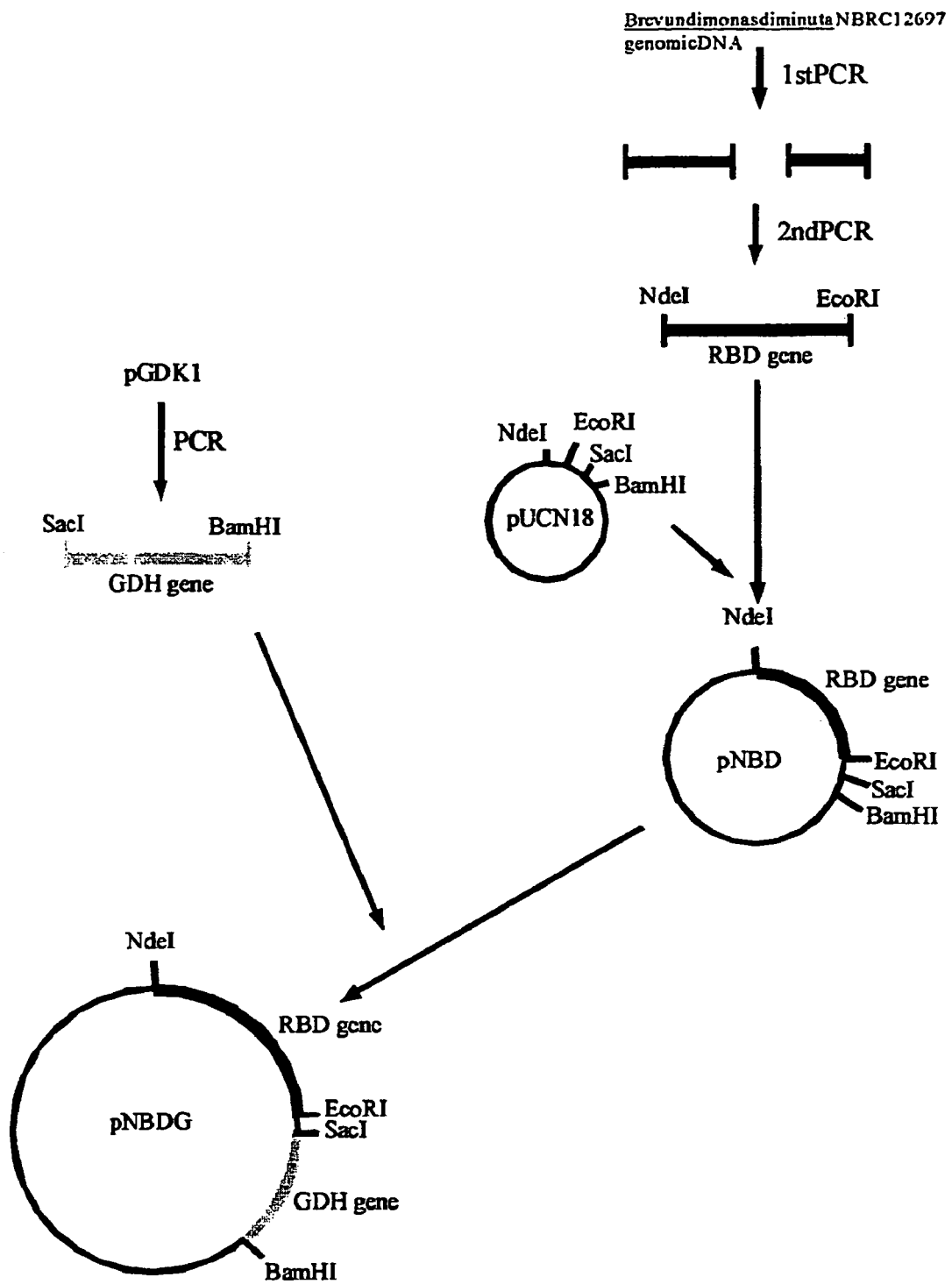

```
                        SEQUENCE LISTING

<160> NUMBER OF SEQ ID NOS: 11

<210> SEQ ID NO 1
<211> LENGTH: 747
<212> TYPE: DNA
<213> ORGANISM: Brevundimonas diminuta

<400> SEQUENCE: 1
atggatcacg acttcgcagg caaggtggcg atcgtcaccg gcgccgcctc gggcatcggc      60
gcggcgacgg cccgcaggct cgcggcctcg ggcgcggcg tcgtggtcgc cgatttcaat     120
catgacggcg cagaggccat cgccgccaag atcggtggag gcgctcgcgc ctgggagatc     180
gatcttggtg acttcgacgc gatcgagcgg atggttggct ggacagtgaa gacgtttggc     240
cggcttgatc tggccgtgaa caacgccggg atcgcggcg attcaaacgg cgtggtcgag     300
```

```
tatgatccga acacgtggcg ccgggtgcag gccgtcaatc tcgacgccat attcggctgc    360
atgaagtatc agattccggc gatgatcgcg tccggcgggg cgccatcgt caatatggcc     420 tccgccttgg ggctcgtcgg ccaacggaac aacgcggcct atatcgcctc caaacacgcg    480
atcatcggcg ccacgaaatc cgcggccttg gattattcgg atcgcggcgt ccgcgtgaat    540
gcgatcgcgc cgggctatat cgacacgccg ctcgtccgca gcgtcgtcag ccaggaggaa    600
ttcgacggga tcgtcgcact ccacccgatc ggtcgcctgg gtaagcccga ggaaatcgcc    660
gatgccgcgg cgttcctgct gtccgatcac gcctcgttcg ttaccggcgc cgtcctggcc    720
gtcgatggcg atatacggc gcaatag                                         747
```

```
<210> SEQ ID NO 2
<211> LENGTH: 248
<212> TYPE: PRT
<213> ORGANISM: Brevundimonas diminuta

<400> SEQUENCE: 2

Met Asp His Asp Phe Ala Gly Lys Val Ala Ile Val Thr Gly Ala Ala
1               5                   10                  15

Ser Gly Ile Gly Ala Ala Thr Ala Arg Arg Leu Ala Ala Ser Gly Ala
            20                  25                  30

Ala Val Val Ala Asp Phe Asn His Asp Gly Ala Glu Ala Ile Ala
        35                  40                  45

Ala Lys Ile Gly Gly Gly Ala Arg Ala Trp Glu Ile Asp Leu Gly Asp
    50                  55                  60

Phe Asp Ala Ile Glu Arg Met Val Gly Trp Thr Val Lys Thr Phe Gly
65                  70                  75                  80

Arg Leu Asp Leu Ala Val Asn Asn Ala Gly Ile Gly Gly Asp Ser Asn
                85                  90                  95

Gly Val Val Glu Tyr Asp Pro Asn Thr Trp Arg Arg Val Gln Ala Val
            100                 105                 110

Asn Leu Asp Ala Ile Phe Gly Cys Met Lys Tyr Gln Ile Pro Ala Met
        115                 120                 125

Ile Ala Ser Gly Gly Gly Ala Ile Val Asn Met Ala Ser Ala Leu Gly
    130                 135                 140

Leu Val Gly Gln Arg Asn Asn Ala Ala Tyr Ile Ala Ser Lys His Ala
145                 150                 155                 160

Ile Ile Gly Ala Thr Lys Ser Ala Ala Leu Asp Tyr Ser Asp Arg Gly
                165                 170                 175

Val Arg Val Asn Ala Ile Ala Pro Gly Tyr Ile Asp Thr Pro Leu Val
            180                 185                 190

Arg Ser Val Val Ser Gln Glu Glu Phe Asp Gly Ile Val Ala Leu His
        195                 200                 205

Pro Ile Gly Arg Leu Gly Lys Pro Glu Glu Ile Ala Asp Ala Ala Ala
    210                 215                 220

Phe Leu Leu Ser Asp His Ala Ser Phe Val Thr Gly Ala Val Leu Ala
225                 230                 235                 240

Val Asp Gly Gly Tyr Thr Ala Gln
                245

<210> SEQ ID NO 3
<211> LENGTH: 20
<212> TYPE: DNA
<213> ORGANISM: Artificial Sequence
<220> FEATURE:
<223> OTHER INFORMATION: Synthetic primer-1
<220> FEATURE:
```

```
<221> NAME/KEY: misc_feature
<222> LOCATION: (15)..(15)
<223> OTHER INFORMATION: n represents a, t, g or c.
<220> FEATURE:
<221> NAME/KEY: misc_feature
<222> LOCATION: (18)..(18)
<223> OTHER INFORMATION: n represents a, t, g or c.

<400> SEQUENCE: 3
tgggarathg ayctnggnga                                        20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer-2
<220> FEATURE:
<221> NAME/KEY: misc_feature
<222> LOCATION: (3)..(3)
<223> OTHER INFORMATION: n represents a, t, g or c.
<220> FEATURE:
<221> NAME/KEY: misc_feature
<222> LOCATION: (15)..(15)
<223> OTHER INFORMATION: n represents a, t, g or c.

<400> SEQUENCE: 4
ggngtrtcda trtanccygg                                        20

<210> SEQ ID NO 5
<211> LENGTH: 358
<212> TYPE: DNA
<213> ORGANISM: Brevundimonas diminuta

<400> SEQUENCE: 5
cttcgacgcg atcgagcgga tggttggctg gacagtgaag acgtttggcc ggcttgatct    60
ggccgtgaac aacgccggga tcggcggcga ttcaaacggc gtggtcgagt atgatccgaa   120
cacgtggcgc cgggtgcagg ccgtcaatct cgacgccata ttcggctgca tgaagtatca   180
gattccggcg atgatcgcgt ccggcggggg cgccatcgtc aatatggcct ccgccttggg   240
gctcgtcggc caacggaaca acgcggccta tatcgcctcc aaacacgcga tcatcggcgc   300
cacgaaatcc gcggccttgg attattcgga tcgcggcgtc cgcgtgaatg cgatcgcg    358

<210> SEQ ID NO 6
<211> LENGTH: 32
<212> TYPE: DNA
<213> ORGANISM: Artificial Sequence
<220> FEATURE:
<223> OTHER INFORMATION: Synthetic primer-3

<400> SEQUENCE: 6
aggacaagca tatggatcac gacttcgcag gc                          32

<210> SEQ ID NO 7
<211> LENGTH: 34
<212> TYPE: DNA
<213> ORGANISM: Artificial Sequence
<220> FEATURE:
<223> OTHER INFORMATION: Synthetic primer-4

<400> SEQUENCE: 7
cagggtgaat tcttactatt gcgccgtata tccg                        34

<210> SEQ ID NO 8
<211> LENGTH: 35
<212> TYPE: DNA
```

```
<213> ORGANISM: Artificial Sequence
<220> FEATURE:
<223> OTHER INFORMATION: Synthetic primer-5

<400> SEQUENCE: 8
agtgcgacga tcccgtcaaa ttcctcctgg ctgac                              35

<210> SEQ ID NO 9
<211> LENGTH: 35
<212> TYPE: DNA
<213> ORGANISM: Artificial Sequence
<220> FEATURE:
<223> OTHER INFORMATION: Synthetic primer-6

<400> SEQUENCE: 9
gtcagccagg aggaatttga cgggatcgtc gcact                              35

<210> SEQ ID NO 10
<211> LENGTH: 33
<212> TYPE: DNA
<213> ORGANISM: Artificial Sequence
<220> FEATURE:
<223> OTHER INFORMATION: Synthetic primer-7

<400> SEQUENCE: 10
caggagctct aaggaggtta acaatgtata aag                                33

<210> SEQ ID NO 11
<211> LENGTH: 28
<212> TYPE: DNA
<213> ORGANISM: Artificial Sequence
<220> FEATURE:
<223> OTHER INFORMATION: Synthetic primer-8

<400> SEQUENCE: 11
cacggatcct tatccgcgtc ctgcttgg                                      28
```

METHOD FOR PRODUCTION OF ERYTHRO-OR THREO-2-AMINO-3-HYDROXYPROPIONIC ACID ESTER, NOVEL CARBONYL REDUCTASE, GENE FOR THE REDUCTASE, VECTOR, TRANSFORMANT, AND METHOD FOR PRODUCTION OF OPTICALLY ACTIVE ALCOHOL USING THOSE

TECHNICAL FIELD

The present invention relates to a method of producing an erythro- or threo-N-Boc-2-amino-3-cyclohexyl-3-hydroxypropionic acid ester, a novel carbonyl reductase, a gene therefor, a vector comprising the gene, a transformant as transformed with the vector, and a method of producing an optically active alcohol using those.

BACKGROUND ART

Optically active N-Boc-2-amino-2-cyclohexyl-3-hydroxypropionic acid esters are compounds useful as starting materials or intermediates for the synthesis of agrochemicals, medicinal chemicals and so forth. Known as a method of producing an optically active N-Boc-2-amino-3-cyclohexyl-3-hydroxypropionic acid ester is the method for the production thereof from unsaturated esters via the Sharpless dihydroxylation reaction (cf. Non-Patent Document 1).

However, any method has not been found out yet for the production of optically active N-Boc-2-amino-3-cyclohexyl-3-hydroxypropionic acid esters by asymmetrically reducing the corresponding N-Boc-2-amino-3-cyclohexyl-3-oxopropionic acid esters.

Non-Patent Document 1: Monica Alonso et al., Organic Process Research & Development, 9, 690-693, 2005

SUMMARY OF THE INVENTION

It is an object of the present invention to provide a novel method of producing the erythro- or threo-N-Boc-2-amino-3-cyclohexyl-3-hydroxypropionic acid ester, a novel carbonyl reductase, a gene therefor, a vector comprising the gene, a transformant as transformed with the vector, and a method of producing an optically active alcohol utilizing those.

The present invention has one or more of the following characteristics.
(1) One characteristic of the present invention relates to a method of producing an erythro-N-Boc-2-amino-3-cyclohexyl-3-hydroxypropionic acid ester,
the method comprising the step of allowing an enzyme source to act on an N-Boc-2-amino-3-cyclohexyl-3-oxopropionic acid ester represented by the formula (1):

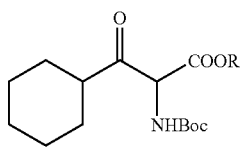

[Chem. 6]

(wherein R is a substituted or unsubstituted alkyl group or aryl group),
the enzyme source having an activity of stereoselectively reducing said compound to the corresponding erythro-N-Boc-2-amino-3-cyclohexyl-3-hydroxypropionic acid ester represented by the formula (2):

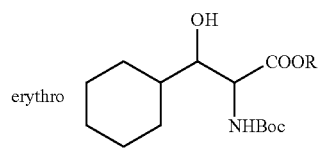

[Chem. 7]

(wherein R is a substituted or unsubstituted alkyl group or aryl group).
(2) Another characteristic of the present invention relates to the method of producing the erythro-N-Boc-2-amino-3-cyclohexyl-3-hydroxypropionic acid ester represented by the formula (2),
the method comprising the step of allowing a microorganism selected from the group consisting of genus *Arthrobacter*, genus *Bacillus*, genus *Brevundimonas*, genus *Corynebacterium*, genus *Oerskovia*, genus *Paenibacillus*, genus *Rhizobium*, genus *Candida*, genus *Debaryomyces*, genus *Pichia*, genus *Rhodotorula*, genus *Saccharomycopsis*, genus *Saturnispora*, genus *Trigonopsis*, genus *Williopsis*, genus *Corynespora* and genus *Plectosphaerella* or a transformant capable of expressing a DNA coding for a polypeptide obtainable from the microorganism to act on the N-Boc-2-amino-3-cyclohexyl-3-oxopropionic acid ester represented by the formula (1).
(3) Another characteristic of the present invention relates to a method of producing a threo-N-Boc-2-amino-3-cyclohexyl-3-hydroxypropionic acid ester,
the method comprising the step of allowing an enzyme source to act on the N-Boc-2-amino-3-cyclohexyl-3-oxopropionic acid ester,
the enzyme source having an activity of stereoselectively reducing the compound to the corresponding threo-N-Boc-2-amino-3-cyclohexyl-3-hydroxypropionic acid ester represented by the formula (3):

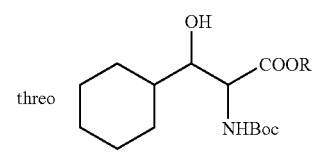

[Chem. 8]

(wherein R is a substituted or unsubstituted alkyl group or aryl group).
(4) Another characteristic of the present invention relates to the method of producing a threo-N-Boc-2-amino-3-cyclohexyl-3-hydroxypropionic acid ester represented by the formula (3),
the method comprising the step of allowing a microorganism selected from the group consisting of genus *Enterobacter*, genus *Morganella*, genus *Pectobacterium*, genus *Circinella*, genus *Emericella*, genus *Eupenicillium* and genus *Hormocomis* to act on the N-Boc-2-amino-3-cyclohexyl-3-oxopropionic acid ester.
(5) Another characteristic of the present invention relates to a polypeptide defined below under (a), (b) or (c):
(a) A polypeptide comprising the amino acid sequence shown in the sequence listing under SEQ ID NO:2;
(b) A polypeptide comprising an amino acid sequence derived from the amino acid sequence shown in the sequence listing under SEQ ID NO:2 by substitution, insertion, deletion and/or addition of one or a plurality of amino acids, said polypeptide having an activity of asymmetrically reducing the N-Boc-2-amino-3-cyclohexyl-3-oxopropionic acid ester to form the corresponding (2R,3R)—N-Boc-2-amino-3-cyclohexyl-3-hydroxypropionic acid ester represented by the formula (4):

[Chem. 9]

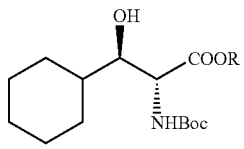

(wherein R is a substituted or unsubstituted alkyl group or aryl group);
(c) A polypeptide comprising an amino acid sequence showing at least 60% sequence homology to the amino acid sequence shown in the sequence listing under SEQ ID NO:2, said polypeptide having an activity of asymmetrically reducing the N-Boc-2-amino-3-cyclohexyl-3-oxopropionic acid ester to form the corresponding (2R,3R)—N-Boc-2-amino-3-cyclohexyl-3-hydroxypropionic acid ester.
(6) Another characteristic of the present invention relates to a DNA defined below under (a), (b) or (c):
(a) A DNA comprising the base sequence shown in the sequence listing under SEQ ID NO:1;
(b) A DNA capable of hybridizing with a DNA having a base sequence complementary to the base sequence shown in the sequence listing under SEQ ID NO:1 under stringent conditions, the DNA coding for a polypeptide having an activity of asymmetrically reducing the N-Boc-2-amino-3-cyclohexyl-3-oxopropionic acid ester to form the corresponding (2R,3R)—N-Boc-2-amino-3-cyclohexyl-3-hydroxypropionic acid ester;
(c) A DNA comprising a base sequence showing at least 60% sequence homology to the base sequence shown in the sequence listing under SEQ ID NO:1, the DNA coding for a polypeptide having an activity of asymmetrically reducing the N-Boc-2-amino-3-cyclohexyl-3-oxopropionic acid ester to form the corresponding (2R,3R)—N-Boc-2-amino-3-cyclohexyl-3-hydroxypropionic acid ester.
(7) Another characteristic of the present invention relates to a vector comprising the DNA.
(8) Another characteristic of the present invention relates to the vector, further comprising a DNA coding for a polypeptide capable of regenerating a reduced-form coenzyme.
(9) Another characteristic of the present invention relates to a transformant obtained by transforming host cells with the vector.
(10) The other characteristic of the present invention relates to a method of producing an optically active alcohol, the method comprising the step of allowing the polypeptide or the transformant to react with a carbonyl group-containing compound.

The invention provides a method of producing an erythro- or threo-N-Boc-2-amino-3-cyclohexyl-3-hydroxypropionic acid ester, a novel carbonyl reductase, a gene therefor, a vector comprising the gene, a transformant as transformed with the vector, and a method of producing a useful optically active alcohol utilizing those.

DETAILED DESCRIPTION OF THE INVENTION

In the following, present invention is described in detail referring to embodiments. These are, however, by no means limitative of the scope of the invention.
1. N-Boc-2-amino-3-cyclohexyl-3-oxopropionic Acid Ester
   An "N-Boc-2-amino-3-cyclohexyl-3-oxopropionic acid ester" of the present invention is a compound represented by the following formula (1):

[Chem. 10]

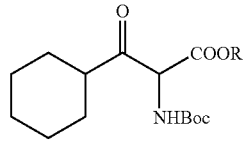

wherein R is a substituted or unsubstituted alkyl group or aryl group. As examples of the alkyl group, there may be mentioned a methyl group, an ethyl group, an isopropyl group, an n-butyl group, an isobutyl group and a tert-butyl group, among others. As examples of the aryl group, there may be mentioned a phenyl group and a naphthyl group, among others. Those compounds can be synthesized by combining appropriate existing methods of chemical synthesis. For example, they can be synthesized by using the techniques described in J. Org. Chem. 1982, 47, 2663 and J. Am. Chem. Soc., 2003, 125, 5139.
2. Method of Producing erythro- or threo-N-Boc-2-amino-3-cyclohexyl-3-hydroxypropionic Acid Ester
   The "method of producing an erythro- or threo-N-Boc-2-amino-3-cyclohexyl-3-hydroxypropionic acid ester" according to the invention comprises the step of allowing an enzyme source having an activity of stereoselectively reducing the compound to act on the N-Boc-2-amino-3-cyclohexyl-3-oxopropionic acid ester, which serves as a substrate. As such an enzyme source, there may be mentioned cells of a microorganism, a polypeptide obtained from the microorganism, or a transformant capable of expressing a DNA coding for the polypeptide.
   Each of the microorganisms enumerated later herein is available to those skilled in the art from various depository institutions. As the depository institutions, there may be mentioned those institutions which correspond to the accession numbers specifying the respective microorganisms. For example, a microorganism specified by an NBRC number is available from the Incorporated Administrative Agency National Institute of Technology and Evaluation Biological Resource Center.
   Microorganisms which can be used in the present production method are not particularly restricted, but in the case of production of an erythro-N-Boc-2-amino-3-cyclohexyl-3-hydroxypropionic acid ester, there may be mentioned, for example, microorganisms belonging to the genera *Arthrobacter, Bacillus, Brevundimonas, Corynebacterium, Oerskovia, Paenibacillus, Rhizobium, Candida, Debaryomyces, Pichia, Rhodotorula, Saccharomycopsis, Saturnispora, Trigonopsis, Williopsis, Corynespora* and *Plectosphaerella*.
   As more preferred microorganisms, there may be mentioned *Arthrobacter paraffineus, Bacillus licheniformis, Bacillus subtilis, Bacillus thuringiensis, Brevundimonas diminuta, Corynebacterium ammoniagenes, Oerskovia turbata, Paenibacillus alvei, Rhizobium radiobacter, Candida magnoliae, Debaryomyces polymorphus, Pichia anomala, Pichia minuta* var. *minuta, Pichia minuta* var. *nonfermentans,*

*Pichia xylosa, Rhodotorula glutinis* var. *dairenensis, Saccharomycopsis fibuligera, Saturnispora saitoi, Trigonopsis variabilis, Williopsis saturnus* var. *mrakii, Corynespora cassiicola, Plectosphaerella cucumerina*, and so forth.

More specifically, there may be mentioned the following ones which are readily available to those skilled in the art: *Arthrobacter paraffineus* ATCC 21218, *Bacillus licheniformis* NBRC 12195, *Bacillus subtilis* ATCC 14593, *Bacillus thuringiensis* NBRC 3951, *Brevundimonas diminuta* NBRC 12697, *Corynebacterium ammoniagenes* NBRC 12072, *Oerskovia turbata* NBRC 15015, *Paenibacillus alvei* NBRC 3343, *Rhizobium radiobacter* NBRC 13264, *Candida magnoliae* NBRC 0705, *Debaryomyces polymorphus* ATCC 20280, *Pichia anomala* NBRC 0120, *Pichia minuta* var. *minuta* NBRC 0975, *Pichia minuta* var. *nonfermentans* NBRC 1473, *Pichia xylosa* NBRC 0950, *Rhodotorula glutinis* var. *dairenensis* NBRC 0415, *Saccharomycopsis fibuligera* NBRC 0104, *Saturnispora saitoi* NBRC 1134, *Trigonopsis variabilis* NBRC 0671, *Williopsis saturnus* var. *mrakii* NBRC 0895, *Corynespora cassiicola* NBRC 30049, *Plectosphaerella cucumerina* NBRC 30005 and so forth.

The microorganisms which can be used in the present production method are not particularly restricted, but in the case of the production of a threo-N-Boc-2-amino-3-cyclohexyl-3-hydroxypropionic acid ester, there may be mentioned, for example, microorganisms belonging to the genera *Enterobacter, Morganella, Pectobacterium, Circinella, Emericella, Eupenicillium, Hormocomis* and so forth.

As more preferred microorganisms, there may be mentioned *Enterobacter aerogenes, Morganella morganii* subsp. *morganii, Pectobacterium carotovorum* subsp. *carotovorum, Circinella umbellata, Emericella unguis, Eupenicillium baarnense*, and *Hormocomis resinae* and so forth.

More specifically, there may be mentioned the following ones which are readily available to those skilled in the art: *Enterobacter aerogenes* NBRC 13534, *Morganella morganii* subsp. *morganii* NBRC 3168, *Pectobacterium carotovorum* subsp. *carotovorum* NBRC 3830, *Pectobacterium carotovorum* subsp. *carotovorum* NBRC 12380, *Pectobacterium carotovorum* subsp. *carotovorum* NBRC 14082, *Circinella umbellata* NBRC 4452, *Emericella unguis* NBRC 8087, *Eupenicillium baarnense* NBRC 6090, *Hormocomis resinae* NBRC 6367 and so forth.

The microorganism and the transformant capable of expressing a DNA coding for a polypeptide obtained from the microorganism, which are to be used in the production method according to the invention, include not only the cultured cells thereof but also treatment products derived therefrom. The term "treatment products" as used herein includes, within the meaning thereof, cells treated with a surfactant or an organic solvent, dried cells, cells treated for disruption and crude cell extracts, for example, and further, immobilization products derived therefrom by conventional means, so long as the activity of asymmetrically reducing the above-mentioned N-Boc-2-amino-3-cyclohexyl-3-oxopropionic acid ester remains. The cultivation of the microorganism and transformant to be used in the production method according to the invention can be carried out using an ordinary liquid nutrient medium containing a carbon source, a nitrogen source, inorganic salts, various nutrients and so forth so long as the microorganism can grow therein.

As one embodiment of the above-mentioned method of producing an optically active N-Boc-2-amino-3-cyclohexyl-3-hydroxypropionic acid ester comprising the step of allowing microbial cells to act on an N-Boc-2-amino-3-cyclohexyl-3-oxopropionic acid ester, there may be mentioned, for example, a method of producing tert-butyl erythro-N-Boc-2-amino-3-cyclohexyl-3-hydroxypropionate comprising the step of allowing the above-mentioned *Brevundimonas diminuta* to act on tert-butyl N-Boc-2-amino-3-cyclohexyl-3-oxopropionate, which is to be described later herein (cf. Example 1).

As one embodiment of the above-mentioned method of producing an optically active N-Boc-2-amino-3-cyclohexyl-3-hydroxypropionic acid ester comprising the step of allowing a transformant capable of expressing a DNA coding for a microorganism-derived polypeptide to act on the N-Boc-2-amino-3-cyclohexyl-3-oxopropionic acid ester, there may be mentioned, for example: a method of producing ethyl (2R, 3R)—N-Boc-2-amino-3-cyclohexyl-3-hydroxypropionate comprising the step of allowing a transformant with a DNA coding for a polypeptide obtained from the above-mentioned *Brevundimonas diminuta* expressed to act on ethyl N-Boc-2-amino-3-cyclohexyl-3-oxopropionate, which is to be described later herein (cf. Example 10); a method of producing ethyl (2R,3R)—N-Boc-2-amino-3-cyclohexyl-3-hydroxypropionate comprising the step of allowing a transformant with a DNA coding for a polypeptide obtained from *Candida magnoliae* expressed to act on ethyl N-Boc-2-amino-3-cyclohexyl-3-oxopropionate (cf. Example 11); and a method of producing ethyl (2S,3S)—N-Boc-2-amino-3-cyclohexyl-3-hydroxypropionate comprising the step of allowing a transformant with a DNA coding for a polypeptide obtained from *Pichia minuta* var. *minuta* expressed to act on ethyl N-Boc-2-amino-3-cyclohexyl-3-oxopropionate (cf. Example 12).

Further, also in microorganisms other than those mentioned above, those skilled in the art will be able to carry out a method of producing an erythro- or threo-N-Boc-2-amino-3-cyclohexyl-3-hydroxypropionic acid ester comprising the step of allowing a transformant expressing a DNA coding for a polypeptide by isolating the polypeptide from a microorganism having an activity of asymmetrically reducing the corresponding N-Boc-2-amino-3-cyclohexyl-3-oxypropionic acid ester, constructing a DNA coding for the polypeptide and growing a transformant expressing the DNA coding for the polypeptide having such an activity.

3. Polypeptide

The "polypeptide", so referred to herein, is a polypeptide capable of reducing a carbonyl group-containing compound to give an optically active alcohol, preferably a polypeptide capable of asymmetrically reducing an N-Boc-2-amino-3-cyclohexyl-3-oxopropionic acid ester to give the corresponding (2R,3R)—N-Boc-2-amino-3-cyclohexyl-3-hydroxypropionic acid ester. Such polypeptide can be isolated from such an organism as a microorganism having the activity in question.

As one embodiment of the polypeptide of the invention, there may be mentioned a polypeptide having the amino acid sequence shown in the sequence listing under SEQ ID NO:2 as encoded by the base sequence shown in the sequence listing under SEQ ID NO:1. Any polypeptide having at least a certain level of sequence homology to the polypeptide having the amino acid sequence shown in the sequence listing under SEQ ID NO:2 and capable of asymmetrically reducing an N-Boc-2-amino-3-cyclohexyl-3-oxopropionic acid ester to give the corresponding (2R,3R)—N-Boc-2-amino-3-cyclohexyl-3-hydroxypropionic acid ester is equivalent to the above-mentioned polypeptide and falls within the scope of the present invention.

The sequence homology, so referred to herein, is expressed as the value of Identity for the overall sequence length as found when two amino acid sequences are comparatively analyzed using, for example, the homology search program FASTA (W. R. Pearson & D. J. Lipman, P.N.A.S. (1988) 85:2444-2448). As the polypeptide having at least a certain level of sequence homology to the polypeptide having the amino acid sequence shown in the sequence listing under SEQ ID NO:2, there may be mentioned polypeptides having 60% or higher, preferably 70% or higher, more preferably 80% or higher, most preferably 85% or higher, sequence homology to the above-mentioned polypeptide.

When subjected to homology search using above-mentioned homology search program FASTA, the amino acid sequence shown in the sequence listing under SEQ ID NO:2 showed about 56% sequence homology to a putative oxidoreductase derived from *Streptomyces coelicolor*. The function of this *Streptomyces coelicolor*-derived enzyme is nothing but a presumed one, and the sequence homology is as low as about 56%. Therefore, according to the common sense among those skilled in the art, it is in general impossible to come to realize, based on the results of homology search in comparison with the above-mentioned *Streptomyces coelicolor*-derived enzyme, that the polypeptide in the practice of the present invention may have optically active alcohol-forming activity.

Such polypeptide can be obtained, for example, by joining a DNA capable of hybridizing under stringent conditions with a DNA having a base sequence complementary to the DNA having the above-mentioned base sequence shown in the sequence listing under SEQ ID NO:1 to an appropriate vector and then introducing the joining product into appropriate host cells for DNA expression. Alternatively, it can also be obtained, for example, by subjecting the polypeptide having the amino acid sequence shown in the sequence listing under SEQ ID NO:2 to treatment for causing amino acid substitution, insertion, deletion or addition according to such an appropriate method known in the art as described in Current Protocols in Molecular Biology (John Wiley and Sons, Inc., 1989), for instance. The number of amino acids to be substituted, inserted, deleted or added is not restricted unless the activity intrinsic in the polypeptide in the practice of the invention is lost; preferably, however, it is not larger than 50, more preferably not larger than 30, still more preferably not larger than 20, most preferably not larger than 10.

The microorganism to serve as the origin of the polypeptide of the invention is not particularly restricted but includes, for example, those microorganisms enumerated hereinabove under 2. As preferred ones, there may be mentioned bacteria belonging to the genus *Brevundimonas* and, as a particularly preferred one, there may be mentioned the *Brevundimonas diminuta* NBRC 12697 strain. This microorganism can be obtained from the Incorporated Administrative Agency National Institute of Technology and Evaluation Department of Biotechnology Biological Resource Center (NBRC: zip code 292-0818, 2-5-8 Kazusakamatari, Kisarazu City, Chiba Prefecture, Japan).

Usable as the medium for cultivating the microorganism to serve as the origin of the polypeptide of the invention are ordinary liquid nutrient media containing a carbon source, a nitrogen source, inorganic salts, organic nutrients and so forth provided that the microorganism can grow therein.

The polypeptide in question can be isolated from the microorganism serving as the origin of the polypeptide of the invention by using an appropriate combination of the protein purification techniques known in the art, for example in the following manner. First, the microorganism is cultured in an appropriate medium, and cells are collected from the culture fluid by centrifugation or filtration. The cells obtained are disrupted by a physical means using a sonicator or glass beads, for instance, and then the cell debris is removed by centrifugation, whereby a cell-free extract is obtained. Then, the polypeptide of the invention is isolated from the cell-free extract by using such techniques as salting out (precipitation with ammonium sulfate, precipitation with sodium phosphate, etc.), solvent-caused precipitation (fractional protein precipitation with acetone or ethanol, for instance), dialysis, gel filtration chromatography, ion exchange chromatography, reversed phase chromatography, ultrafiltration and so forth, either alone or in combination.

4. DNA

The "DNA", so referred herein, is a DNA coding for the above-mentioned polypeptide of the invention and may be any one that can express that polypeptide in host cells harboring the DNA introduced therein by the method to be described later herein; it may contain any untranslated region. Once the polypeptide in question has been obtained, those skilled in the art can obtain the DNA of the invention from the microorganism which is the source of the polypeptide in the conventional manner, for example by the method described below.

First, the polypeptide of the invention as isolated is digested with an appropriate endopeptidase, and the resulting peptide fragments are separated by reversed phase HPLC. Then, the amino acid sequences of these peptide fragments are determined partly or wholly using, for example, a model ABI 492 protein sequencer (product of Applied Biosystems).

Based on the thus-obtained amino acid sequence information, PCR (Polymerase Chain Reaction) primers for amplifying a part of the DNA coding for the polypeptide are synthesized. Then, the chromosomal DNA of the microorganism which is the origin of the polypeptide, or cDNA, is prepared by the conventional DNA isolation method. Using this DNA as a template, the PCR is carried out with the above-mentioned PCR primers and a part of the DNA coding for the polypeptide is thus amplified, and the base sequence thereof is determined. The base sequence can be determined by using a model ABI 373A DNA sequencer (product of Applied Biosystems), for example.

Once the base sequence of that part of the DNA coding for the polypeptide in question has been revealed, the sequence of the whole thereof can be determined by the i-PCR method (Nucl. Acids Res., 16, 8186 (1988)), for example.

As an embodiment of the DNA of the present invention which can be obtained in this manner, there may be mentioned the DNA comprising the base sequence shown in the sequence listing under SEQ ID NO:1. Further, any DNA having at least a certain level of sequence homology to the base sequence shown in the sequence listing under SEQ ID NO:1 and coding for a polypeptide capable of asymmetrically reducing an N-Boc-2-amino-3-cyclohexyl-3-oxopropionic acid ester to give the corresponding (2R,3R)—N-Boc-2-amino-3-cyclohexyl-3-hydroxypropionic acid ester is equivalent to the above-mentioned DNA and falls within the scope of the present invention.

The base sequence homology, so referred to herein, is expressed as the value of Identity for the overall sequence length as found when two base sequences are comparatively analyzed using, for example, the homology search program FASTA (W. R. Pearson & D. J. Lipman, P.N.A.S. (1988) 85:2444-2448). As the DNA having at least a certain level of sequence homology to the DNA having the base sequence shown in the sequence listing under SEQ ID NO:1, there may be mentioned DNAs having 60% or higher, preferably 70% or higher, more preferably 80% or higher, most preferably 85% or higher, sequence homology to the above-mentioned DNA.

The DNA of the invention further includes any DNA capable of hybridizing with a DNA having a base sequence complementary to the base sequence shown in the sequence listing under SEQ ID NO:1 under stringent conditions and coding for a polypeptide capable of asymmetrically reducing an N-Boc-2-amino-3-cyclohexyl-3-oxopropionic acid ester to give the corresponding (2R,3R)—N-Boc-2-amino-3-cyclohexyl-3-hydroxypropionic acid ester. Furthermore, the DNA of the invention includes a DNA capable of hybridizing with a base sequence complementary to the base sequence shown under SEQ ID NO:1 under stringent conditions and coding for a polypeptide capable of reducing a carbonyl group-containing compound to give an optically active alcohol.

The DNA capable of hybridizing with a DNA having a base sequence complementary to the base sequence shown in the sequence listing under SEQ ID NO:1 under stringent conditions is a DNA with which a DNA having a base sequence complementary to the base sequence shown in the sequence listing under SEQ ID NO:1 specifically hybridizes when a colony hybridization method, plaque hybridization method, Southern hybridization method or the like is carried out.

The "stringent conditions" so referred to herein are, for example, those conditions such that the hybridization is carried out in an aqueous solution comprising 75 mM trisodium citrate, 750 mM sodium chloride, 0.5% sodium dodecyl sulfate, 0.1% bovine serum albumin, 0.1% polyvinylpyrrolidone and 0.1% Ficoll 400 (product of Amersham Biosciences) at 65° C., followed by washing with an aqueous solution containing 15 mM trisodium citrate, 150 mM sodium chloride and 0.1% sodium dodecyl sulfate at 60° C. Preferred are those conditions such that the hybridization carried out under the above conditions is followed by washing with an aqueous solution containing 15 mM trisodium citrate, 150 mM sodium chloride and 0.1% sodium dodecyl sulfate at 65° C., more preferably followed by washing with an aqueous solution containing 1.5 mM trisodium citrate, 15 mM sodium chloride and 0.1% sodium dodecyl sulfate at 65° C. The gene manipulation procedures described herein, including the above-mentioned DNA isolation and the vector preparation, transformation and other procedures which are described later herein, can be carried out as described in such a monograph as Molecular Cloning, 2nd Edition (Cold Spring Harbor Laboratory Press, 1989) unless otherwise specified. The "%" used herein, unless otherwise specified, means "% (w/v)".

5. Vector

The "vector", so referred to herein, is not particularly restricted provided that it allows the gene encoded by the above-mentioned DNA to be expressed in appropriate host cells. As such vector, there may be mentioned, for example, a plasmid vector, a phage vector and a cosmid vector; further, a shuttle vector capable of gene exchange with another host strain can also be used.

Each of such vectors generally contains a regulatory factor such as a lacUV5 promoter, trp promoter, trc promoter, tac promoter, lpp promoter, tufB promoter, recA promoter and pL promoter and can be suitably used as an expression vector containing an expression unit operably joined to the DNA of the invention. For example, pUCN18 as described later herein can be suitably used.

The term "regulatory factor" refers to a base sequence containing a functional promoter and any pertinent transcription elements (e.g. enhancer, CCAAT box, TATA box, SPI site, etc.).

The phrase "operably joined" means that various regulatory elements, such as the promoter and enhancer, which regulate the expression of the gene, are joined to the gene in such a condition that they can operate in host cells. The fact that the type and sort of regulatory factor may vary according to the host are well known to those skilled in the art. As an example of the vector of the invention, there may be mentioned the plasmid pNBD which is to be described later herein and is obtained by introduction of a DNA having a base sequence derived from the base sequence shown under SEQ ID NO:1 by substitution of T for the 603rd C into the above-mentioned pUCN18 (cf. Example 6).

6. Host Cells

As the host cells so referred to herein, there may be mentioned bacteria, yeasts, filamentous fungi, plant cells and animal cells, among others; from the viewpoint of introduction and expression efficiency, however, bacteria are preferred, and *Escherichia coli* is particularly preferred. The vector containing the DNA of the invention can be introduced into host cells by a method known in the art. In the case of using *Escherichia coli* cells as the host cells, the vector can be introduced into the host cells using, for example, commercially available *E. coli* HB101 competent cells (product of Takara Bio Inc.).

7. Transformant

The "transformant", so referred to herein, is obtained by inserting the DNA coding for the polypeptide of the invention into the above-mentioned vector and introducing the resulting vector into the host cells. The "transformant" of the invention includes not only the cultured cells thereof but also treatment products derived therefrom. The term "treatment products" as used herein includes, within the meaning thereof, cells treated with a surfactant or an organic solvent, dried cells, cells treated for disruption and crude cell extracts, for example, and, further, immobilization products derived from them by conventional means, so long as the activity of asymmetrically reducing the above-mentioned N-Boc-2-amino-3-cyclohexyl-3-oxopropionic acid ester remains. The cultivation of the transformant of the invention can be carried out using an ordinary liquid nutrient medium containing a carbon source, a nitrogen source, inorganic salts, organic nutrients and so forth so long as the microorganism can grow therein.

As an example of the transformant of the invention, there may be mentioned *E. coli* HB101 (pNBD) to be described later herein (cf. Example 8).

8. Method of Producing Optically Active Alcohol

The "production of optically active alcohols" according to the invention can be carried out by adding, to an appropriate solvent, a carbonyl group-containing compound to serve as the substrate and the polypeptide of the invention or the transformant harboring the vector containing the DNA coding for the polypeptide as introduced therein. If necessary, a coenzyme such as NADH may be added. An aqueous solvent or a mixture of an aqueous solvent and an organic solvent may be used for the reaction. As the organic solvent, there may be mentioned, for example, toluene, ethyl acetate, n-butyl acetate, hexane, isopropanol, diisopropyl ether, methanol, acetone and dimethyl sulfoxide. The reaction is carried out, for example, at a temperature of 10° C. to 700, and the pH of the reaction mixture is maintained at −4-10, for instance. The reaction can be carried out in a batch wise or continuous manner. In the case of batchwise operation, the reaction substrate is added at a charge concentration of 0.1% to 70% (w/v).

As the "carbonyl group-containing compound" to serve as the substrate, there may be mentioned, for example, ethyl N-Boc-2-amino-3-cyclohexyl-3-oxopropionate and the like; however, it is not particularly restricted but includes all other carbonyl compounds that can be reduced and thus converted to an "optically active alcohol" under the reaction conditions mentioned above.

The reaction product optically active alcohol can be purified in the conventional manner. For example, it can be purified by extracting the reaction mixture containing the optically active alcohol as resulting from the reaction with an organic solvent such as ethyl acetate or toluene, then distilling off the organic solvent under reduced pressure and subjecting the residue to such treatment as distillation, recrystallization or chromatography.

9. Modification Example of Method of Producing Optically Active Alcohol

By bringing the polypeptide of the invention or the transformant harboring the vector containing the DNA coding for the polypeptide as introduced therein into contact with a carbonyl group-containing compound, if necessary in the presence of a coenzyme such as NADH, and thus allowing the reaction to proceed, it is possible to asymmetrically reduce the carbonyl group-containing compound to give an optically active alcohol. On this occasion, such a coenzyme as NADH is converted to the oxidized form as the reaction proceeds. By carrying out the reaction between the compound to serve as the substrate for the polypeptide and the polypeptide of the invention in the presence of a polypeptide having ability to convert the oxidized form coenzyme to the reduced form (such ability is hereinafter referred to as "coenzyme regenerating ability"), it becomes possible to reduce the coenzyme usage. Usable as the polypeptide having coenzyme regenerating ability are, for example, hydrogenase, formate dehydrogenase, alcohol dehydrogenase, aldehyde dehydrogenase, glucose-6-phosphate dehydrogenase and glucose dehydrogenase. Among them, glucose dehydrogenase is preferably used.

As an example of the vector containing the DNA coding for the polypeptide of the invention and the DNA coding for a polypeptide having coenzyme regenerating ability both inserted therein, there may be mentioned the pNBDG, which is to be described later herein, resulting from insertion of a *Bacillus megaterium*-derived glucose dehydrogenase gene into the above-mentioned expression vector pNBD (cf. Example 7).

A transformant harboring both the DNA coding for the polypeptide of the invention and the DNA coding for a polypeptide having reduced form coenzyme regenerating ability can be obtained by inserting both the DNA coding for the polypeptide of the invention and the DNA coding for a polypeptide having coenzyme regenerating ability into one and the same vector and introducing the resulting vector into host cells or, alternatively, inserting these two DNAs respectively into two vectors differing in incompatibility group and introducing the two vectors into the same host cells. As an example of the transformant harboring the DNA coding for the polypeptide of the invention and the DNA coding for a polypeptide having coenzyme regenerating ability, there may be mentioned the *E. coli* HB101 (pNBDG) described later herein, which can be obtained by transforming *E. coli* HB101 with the above-mentioned pNBDG (cf. Example 8).

The cultivation of the transformant harboring both the DNA coding for the polypeptide of the invention and the DNA coding for a polypeptide having coenzyme regenerating ability can be carried out using an ordinary liquid nutrient medium containing a carbon source, a nitrogen source, inorganic salts, various nutrients and so forth so long as the transformant can grow therein.

In the case of producing an optically active alcohol using the polypeptide of the invention and the polypeptide having coenzyme regenerating ability in combination, the polypeptide having coenzyme regenerating ability (e.g. glucose dehydrogenase) and a compound to serve as the substrate thereof (e.g. glucose) are further added to the above reaction composition. By using a transformant harboring both the DNA coding for the polypeptide of the invention and the DNA coding for a polypeptide having coenzyme regenerating ability, it is also possible to produce an optically active alcohol. Furthermore, the above-mentioned optically active alcohol may also be produced by utilizing both a transformant harboring the DNA coding for the polypeptide of the invention and a transformant harboring the DNA coding for a polypeptide having coenzyme regenerating ability.

In particular, when a transformant harboring both the DNA coding for the polypeptide of the invention and the DNA coding for a polypeptide having coenzyme regenerating ability or a treatment product derived therefrom is used, it is unnecessary to separately add the polypeptide having coenzyme regenerating ability (e.g. glucose dehydrogenase) and the optically active alcohol production can be carried out efficiently.

When *E. coli* HB101 (PNBDG), one of the embodiments of the present invention, is added and ethyl N-Boc-2-amino-3-cyclohexyl-3-oxopropionate is used as the substrate under the reaction conditions mentioned above, ethyl (2R,3R)—N-Boc-2-amino-3-cyclohexyl-3-hydroxypropionate is obtained (cf. Example 10).

As mentioned hereinabove, the polypeptide of the invention can be produced efficiently according to the invention, and an excellent method of producing useful optically active alcohols, typically ethyl (2R,3R)—N-Boc-2-amino-3-cyclohexyl-3-hydroxypropionate, for instance, is provided by utilizing the polypeptide.

BRIEF DESCRIPTION OF THE DRAWING

FIG. 1 shows a construction method and a structure of a recombinant vector pNBDG.

BEST MODE FOR CARRYING OUT THE INVENTION

The following examples illustrate the invention in detail. They are, however, by no means limitative of the scope of the invention. The detailed procedures concerning the recombinant DNA technology as used in the following examples are described in the following monographs:
Molecular Cloning 2nd Edition (Cold Spring Harbor Laboratory Press, 1989); and Current Protocols in Molecular Biology (Greene Publishing Associates and Wiley-Interscience).

Each of the microorganisms described in each example is available to those skilled in the art from various depository institutions. As the depository institutions, there may be mentioned those institutions which correspond to the accession numbers specifying the respective microorganisms. For example, a microorganism specified by an NBRC number is available from the Incorporated Administrative Agency National Institute of Technology and Evaluation Biological Resource Center.

SYNTHESIS EXAMPLE 1

To 18.1 g of benzophenone imine were added 20 g of glycine tert-butyl ester hydrochloride and 100 ml of methylene chloride, and the mixture was stirred at room temperature for 62 hours. Distilled water (100 ml) was added and, after phase separation, the organic layer was concentrated and dried under reduced pressure to give 28.8 g of a glycine derivative. A THF solution (140 ml) of this compound was added dropwise to a THF solution (60 ml) containing 10.9 g of KOtBu at −70° C. Thereafter, this solution was added dropwise to a THF solution (50 ml) containing 14.2 g of cyclohexanecarbonyl chloride at −78° C. and, then, the mixture was stirred for 1 hour. Thereto was added 150 ml of 1 M citric acid, and the mixture was stirred at room temperature for 15 hours. The THF was removed by concentration under reduced pressure, the residue was extracted with ethyl acetate, and 100 ml of ethanol, 61.7 g of $Na_2CO_3$ and 23.3 g of $Boc_2O$ were added to the aqueous layer obtained and the mixture was stirred at room temperature for 2 hours. The white solid was removed by filtration, the filtrate was extracted with ethyl acetate, and the organic layer was concentrated and dried under reduced pressure to give 26.2 g of a yellow oily substance. This was purified on a silica gel column, whereby 7.5 g of tert-butyl N-Boc-2-amino-3-cyclohexyl-3-oxopropionate.

EXAMPLE 1

Production of Tert-butyl Erythro- or Threo-N-Boc-2-amino-3-cyclohexyl-3-hydroxypropionate Using Bacterial Cells In each large test tube, there was prepared 5 ml of a liquid medium (pH 7) having the following composition: 10 g of meat extract, 10 g of peptone, 5 g of yeast extract and 3 g of NaCl (per liter). The medium was steam-sterilized at 120° C. for 20 minutes. This medium was inoculated with one loopful of cells, cultured in advance in the same medium on a plate, of one of *Arthrobacter paraffineus* ATCC 21218, *Bacillus licheniformis* NBRC 12195, *Bacillus subtilis* ATCC 14593, *Bacillus thuringiensis* NBRC 3951, *Brevundimonas diminuta* NBRC 12697, *Corynebacterium ammoniagenes* NBRC 12072, *Enterobacter aerogenes* NBRC 13534, *Morganella morganii* subsp. *morganii* NBRC 3168, *Oerskovia turbata* NBRC 15015, *Paenibacillus alvei* NBRC 3343, *Pectobacterium carotovorum* subsp. *carotovorum* NBRC 3830, *Pectobacterium carotovorum* subsp. *carotovorum* NBRC 12380, *Pectobacterium carotovorum* subsp. *carotovorum* NBRC 14082 or *Rhizobium radiobacter* NBRC 13264, followed by 24 to 72 hours of shake culture at 30° C.

Each culture fluid obtained was subjected to centrifugation, and the cells collected were suspended in 1 ml of 0.1 M phosphate buffer (pH 6.5).

The 1-ml cell suspension obtained was placed in a test tube and, further, there were added 5 mg of glucose and 0.5 mg of tert-butyl N-Boc-2-amino-3-cyclohexyl-3-oxopropionate, and the reaction was allowed to proceed at 30° C. for 24 hours with shaking. After the reaction, 1 ml of ethyl acetate was added and extraction was carried out. The quantitation of tert-butyl N-Boc-2-amino-3-cyclohexyl-3-hydroxypropionate and the determination of the threo/erythro ratio thereof were carried out by capillary gas chromatography (column: GL Sciences InertCAP 5 (ID 0.25 mm×30 m), column temperature: 200° C., carrier gas: helium (70 kPa), detection: FID). The results thus obtained are shown in Table 1.

TABLE 1

Bacteria capable of asymmetrically reducing tert-butyl N-Boc-2-amino-3-cyclohexyl-3-oxopropionate

| genus | species | No. | product concentration (ppm) | absolute configuration |
| --- | --- | --- | --- | --- |
| *Arthrobacter* | *paraffineus* | ATCC 21218 | trace | erythro |
| *Bacillus* | *licheniformis* | NBRC 12195 | trace | erythro |
| *Bacillus* | *subtilis* | ATCC 14593 | trace | erythro |
| *Bacillus* | *thuringiensis* | NBRC 3951 | trace | erythro |
| *Brevundimonas* | *diminuta* | NBRC 12697 | 24 | erythro |
| *Corynebacterium* | *ammoniagenes* | NBRC 12072 | trace | erythro |
| *Enterobacter* | *aerogenes* | NBRC 13534 | trace | threo |
| *Morganella* | *morganii* subsp. *morganii* | NBRC 3168 | trace | threo |
| *Oerskovia* | *turbata* | NBRC 15015 | trace | erythro |
| *Paenibacillus* | *alvei* | NBRC 3343 | trace | erythro |
| *Pectobacterium* | *carotovorum* subsp. *carotovorum* | NBRC 3830 | trace | threo |
| *Pectobacterium* | *carotovorum* subsp. *carotovorum* | NBRC 12380 | 25 | threo |
| *Pectobacterium* | *carotovorum* subsp. *carotovorum* | NBRC 14082 | 18 | threo |
| *Rhizobium* | *radiobacter* | NBRC 13264 | trace | erythro | trace: a very small amount

EXAMPLE 2

Production of Tert-butyl erythro-N-Boc-2-amino-3-cyclohexyl-3-hydroxypropionate Using Yeast Cells In each large test tube, there was prepared 5 ml of a liquid medium (pH 7) having the following composition: 40 g of glucose, 3 g of yeast extract, 7 g of $KH_2PO_4$, 13 g of $(NH_4)_2HPO_4$, 1 g of NaCl, 0.8 g of $MgSO_4 \cdot 7H_2O$, 60 mg of $ZnSO_4 \cdot 7H_2O$, 90 mg of $FeSO_4 \cdot 7H_2O$, 5 mg of $CuSO_4 \cdot 5H_2O$ and 10 mg of $MnSO_4 \cdot 4\text{-}6H_2O$ (per liter). The medium was steam-sterilized at 120° C. for 20 minutes. This medium was inoculated with one loopful of cells, cultured in advance on an agar medium (pH 7) having the composition comprising 200 g of malt extract and 20 g of agar (per liter), of one of *Candida magnoliae* NBRC 0705, *Debaryomyces polymorphus* ATCC 20280, *Pichia anomala* NBRC 0120, *Pichia minuta* var. *minuta* NBRC 0975, *Pichia minuta* var. *nonfermentans* NBRC 1473, *Pichia xylosa* NBRC 0950, *Rhodotorula glutinis* var. *dairenensis* NBRC 0415, *Saccharomycopsis fibuligera* NBRC 0104, *Saturnispora saitoi* NBRC 1134, *Trigonopsis variabilis* NBRC 0671 or *Williopsis saturnus* var. *mrakii* NBRC 0895, followed by 24 to 72 hours of shake culture at 30° C.

Each culture fluid obtained was subjected to centrifugation, and the cells collected were suspended in 1 ml of 0.1 M phosphate buffer (pH 6.5).

The 1-ml cell suspension obtained was placed in a test tube and, further, there were added 5 mg of glucose and 0.5 mg of tert-butyl N-Boc-2-amino-3-cyclohexyl-3-oxopropionate, and the reaction was allowed to proceed at 30° C. for 24 hours with shaking. After the reaction, 1 ml of ethyl acetate was added and extraction was carried out. The quantitation of tert-butyl N-Boc-2-amino-3-cyclohexyl-3-hydroxypropionate and the determination of the threo/erythro ratio thereof were carried out in the same manner as in Example 1. The results thus obtained are shown in Table 2.

TABLE 2

Yeasts capable of asymmetrically reducing tert-butyl
N-Boc-2-amino-3-cyclohexyl-3-oxopropionate

| genus | species | No. | product concentration (ppm) | absolute configuration |
|---|---|---|---|---|
| Candida | magnoliae | NBRC 0705 | trace | erythro |
| Debaryomyces | polymorphus | ATCC20280 | 689 | erythro |
| Pichia | minuta var. minuta | NBRC 0975 | trace | erythro |
| Pichia | minuta var. nonfermentans | NBRC 1473 | 16 | erythro |
| Pichia | anomala | NBRC 0120 | 25 | erythro |
| Pichia | xylosa | NBRC 0950 | trace | erythro |
| Rhodotorula | glutinis var. dairenensis | NBRC 0415 | 82 | erythro |
| Saccharomycopsis | fibuligera | NBRC 0104 | 37 | erythro |
| Saturnispora | saitoi | NBRC 1134 | trace | erythro |
| Trigonopsis | variabilis | NBRC 0671 | 106 | erythro |
| Williopsis | saturnus var. mrakii | NBRC 0895 | trace | erythro | trace: a very small amount

TABLE 3

Fungi capable of asymmetrically reducing tert-butyl
N-Boc-2-amino-3-cyclohexyl-3-oxopropionate

| genus | species | No. | product concentration (ppm) | absolute configuration |
|---|---|---|---|---|
| Circinella | umbellata | NBRC 4452 | 23 | threo |
| Hormocomis | resinae | NBRC 6367 | 30 | threo |
| Corynespora | cassiicola | NBRC 30049 | 33 | erythro |
| Emericella | unguis | NBRC 8087 | 48 | threo |
| Eupenicillium | baarnense | NBRC 6090 | 90 | threo |
| Plectosphaerella | cucumerina | NBRC 30005 | 39 | erythro |

EXAMPLE 3

Production of Tert-butyl erythro- or Threo-N-Boc-2-amino-3-cyclohexyl-3-hydroxypropionate Using Fungal Cells In each large test tube, there was prepared 5 ml of a liquid medium (pH 7) having the following composition: 10 g of glucose, 10 g of polypeptone, 10 g of meat extract, 5 g of yeast extract, 1 g of NaCl and 0.5 g of $MgSO_4·7H_2O$ (per liter). The medium was steam-sterilized at 120° C. for 20 minutes. This medium was inoculated with one loopful of cells, cultured in advance on an agar medium (pH 6.2) having the composition comprising 60 g of malt extract and 20 g of agar (per liter), of one of *Circinella umbellata* NBRC 4452, *Emericella unguis* NBRC 8087, *Eupenicillium baarnense* NBRC 6090, *Hormocomis resinae* NBRC 6367, *Corynespora cassiicola* NBRC 30049 and *Plectosphaerella cucumerina* NBRC 30005, followed by 24 to 72 hours of shake culture at 30° C.

Each culture fluid obtained was subjected to filtration, and the cells collected were suspended in 1 ml of 0.1 M phosphate buffer (pH 6.5).

The 1-ml cell suspension obtained was placed in a test tube and, further, there were added 5 mg of glucose and 0.5 mg of tert-butyl N-Boc-2-amino-3-cyclohexyl-3-oxopropionate, and the reaction was allowed to proceed at 30° C. for 24 hours with shaking. After the reaction, 1 ml of ethyl acetate was added and extraction was carried out. The quantitation of tert-butyl N-Boc-2-amino-3-cyclohexyl-3-hydroxypropionate and the determination of the threo/erythro ratio thereof were carried out in the same manner as in Example 1. The results thus obtained are shown in Table 3.

EXAMPLE 4

Polypeptide Purification

A polypeptide capable of asymmetrically reducing ethyl N-Boc-2-amino-3-cyclohexyl-3-oxopropionate to give (2R, 3R)—N-Boc-2-amino-3-cyclohexyl-3-hydroxypropionate was separated and purified to a single compound from the *Brevundimonas diminuta* NBRC 12697 strain according to the following method. Unless otherwise specified, the purification procedure was carried out at 4° C.

The reducing activity against ethyl N-Boc-2-amino-3-cyclohexyl-3-oxopropionate was calculated in the following manner. First, an appropriate amount of a crude enzyme solution and 100 mM phosphate buffer (pH 6.5) were added to a test tube to make a total volume of 0.5 ml. Further, 0.25 mg of ethyl N-Boc-2-amino-3-cyclohexyl-3-oxopropionate and 1 mg of NADH were added, and the reaction was allowed to proceed at 30° C. for 2 hours with shaking. After the reaction, 1 ml of ethyl acetate was added and extraction was carried out. The quantitation of the product ethyl N-Boc-2-amino-3-cyclohexyl-3-hydroxypropionate was carried by capillary gas chromatography (column: GL Sciences InertCAP 5 (ID 0.25 mm×30 m), column temperature: 200° C.; carrier gas: helium (70 kPa), detection: FID). The enzyme activity was calculated from the amount of the ethyl N-Boc-2-amino-3-cyclohexyl-3-hydroxypropionate formed. The activity such that 1 μmol of ethyl N-Boc-2-amino-3-cyclohexyl-3-hydroxypropionate is formed in 1 minute under the reaction conditions mentioned above is defined as 1 unit.

(Microorganism Cultivation)

In a 5-L jar fermenter (product of B.E. Marubishi Co. Ltd.), there was prepared 3 L of a liquid medium (pH 7) having the following composition: 10 g of meat extract, 10 g of peptone, 5 g of yeast extract, 3 g of sodium chloride and 0.1 g of Adekanol LG-109 (product of NOF Corp.). The medium was steam-sterilized at 120° C. for 20 minutes. This medium was inoculated with 15 ml of a culture fluid prepared by preculture of the *Brevundimonas diminuta* NBRC 12697 strain in the same medium, and the microorganism was cultured at 30° C. for 16 hours at a stirring rate of 450 rpm and an aeration rate of 0.9 NL/min.

(Cell-Free Extract Preparation)

Cells were collected from the above culture fluid by centrifugation, and the cells were washed with a 0.8% aqueous solution of sodium chloride. These cells were suspended in 10 mM phosphate buffer (pH 7.0) containing 5 mM β-mercaptoethanol and disrupted using a model SONIFIER 250 sonicator (product of Branson Ultrasonics Corp.) and, then, the cell debris was removed by centrifugation to give a cell-free extract.

(DEAE-TOYOPEARL Column Chromatography)

The above cell-free extract was applied to a DEAE-TOYOPEARL 650M (product of Tosoh Corporation) column (400 ml) equilibrated in advance with 10 mM phosphate buffer (pH 7.0) containing 5 mM β-mercaptoethanol for active fraction adsorption. The column was washed with the same buffer and then the active fraction was eluted with a linear gradient of NaCl (from 0 M to 0.3 M).

(Phenyl-TOYOPEARL Column Chromatography)

Ammonium sulfate and glycerol were dissolved in the active fraction obtained by DEAE-TOYOPEARL column chromatography to respective final concentrations of 1.0 M and 10%, and the resulting solution was applied to a Phenyl-TOYOPEARL 650M (product of Tosoh Corporation) column (50 ml) equilibrated in advance with 10 mM phosphate buffer (pH 7.0) containing 1.0 M ammonium sulfate and 5 mM β-mercaptoethanol and 10% glycerol for active fraction adsorption. The column was washed with the same buffer and then the active fraction was eluted with a linear gradient of ammonium sulfate (from 1.0 M to 0 M). The active fractions were collected and dialyzed overnight against 10 mM phosphate buffer (pH 7.0) containing 5 mM β-mercaptoethanol and 10% glycerol.

(5'-AMP Sepharose Column Chromatography)

The active fraction obtained by Phenyl-TOYOPEARL column chromatography was applied to a 5'-AMP Sepharose6 4B (product of Amersham Biosciences) column (14 ml) equilibrated in advance with 10 mM phosphate buffer containing 5 mM β-mercaptoethanol and 10% glycerol for active fraction adsorption. The column was washed with the same buffer and then the active fraction was eluted with a linear gradient of NaCl (from 0 M to 2 M), and a purified, electrophoretically single polypeptide preparation was obtained.

EXAMPLE 5

Gene cloning (Construction of PCR Primer)

The purified polypeptide obtained in Example 4 was denatured in the presence of 8 M urea and digested with *Achromobacter*-derived lysyl endopeptidase (product of Wako Pure Chemical Industries), and the amino acid sequence of a peptide fragment obtained was determined using a model ABI 492 protein sequencer (product of Applied Biosystems). Based on a DNA sequence deduced from this amino acid sequence, primer 1: 5'-TGGGARATHGAYCTNGGNGA-3' (SEQ ID NO:3) and primer 2: 5'-GGNGTRTCDATRTANC-CYGG-3' (SEQ ID NO:4) were synthesized for amplifying a part of the gene coding for the polypeptide in question by PCR.

(Gene Amplification by PCR)

Using the G NOME$^R$ DNA KIT (product of B-BIO gene) and following the instruction manual attached thereto, a chromosomal DNA was extracted from cells of the *Brevundimonas diminuta* NBRC 12697 strain cultured in the same manner as in Example 4. Then, using the DNA primers 1 and 2 prepared as described above and using the chromosomal DNA as the template, PCR was carried out, whereupon an about 0.4 kbp DNA fragment considered to be a part of the desired gene was amplified. The PCR was carried out using TaKaRa Ex Taq (product of Takara Bio Inc.) as a DNA polymerase, and the reaction conditions were established according to the instruction manual attached thereto. This DNA fragment was subjected to direct sequencing using the ABI PRISM Dye Terminator Cycle Sequencing Ready Reaction Kit (product of Perkin Elmer) and ABI 373A DNA Sequencer (product of Perkin Elmer), and the base sequence thereof was analyzed. The base sequence revealed as a result of the analysis is shown in the sequence listing under SEQ ID NO:5.

(Determination of Full-Length Sequence of Desired Gene by i-PCR)

The chromosomal DNA of the *Brevundimonas diminuta* NBRC 12697 strain as prepared above was completely digested with the restriction enzyme BamHI, and the DNA fragment mixture obtained was subjected to intramolecular cyclization using T4 ligase. Using this cyclization product as the template, the whole base sequence of the gene containing the above-mentioned base sequence shown under SEQ ID NO:5 was determined by the i-PCR method (Nucl. Acids Res., 16, 8186 (1988)). The result is shown in the sequence listing under SEQ ID NO:1. The i-PCR was carried out using TaKaRa LA Taq (product of Takara Bio Inc.) as a DNA polymerase and the reaction conditions were established according to the instruction manual attached thereto. The amino acid sequence encoded by the base sequence shown under SEQ ID NO:1 is shown under SEQ ID NO:2.

EXAMPLE 6

Construction of Expression Vector

Using primer 3: 5'-AGGACAAGCATATGGATCAC-GACTTCGCAGGC-3' (SEQ ID NO:6 in the sequence listing), primer 4: 5'-CAGGGTGAATTCTTACTATTGCGC-CGTATATCCG-3' (SEQ ID NO:7 in the sequence listing), primer 5: 5'-AGTGCGACGATCCCGTCAAATTCCTC-CTGGCTGAC-3' (SEQ ID NO:8 in the sequence listing) and primer 6: 5'-GTCAGCCAGGAGGAATTTGACGG-GATCGTCGCACT-3' (SEQ ID NO: 9 in. the sequence listing) and using, as the template, the chromosomal DNA of the *Brevundimonas diminuta* NBRC 12697 strain as obtained in Example 5, PCR was carried out. The combination of primers 3 and 5 and the combination of primers 4 and 6 gave about 0.6 kbp and 0.2 kbp double-stranded DNAs, respectively. Then, these double-stranded DNAs were mixed together, and PCR was carried out using the mixture as the template and using primers 3 and 4 in combination. As a result, there was obtained a double-stranded DNA comprising a gene having a base sequence derived from the base sequence shown in the sequence listing under SEQ ID NO:1 by substitution of T for the 603rd C in that sequence to destruct the relevant EcoRI site, with an NdeI recognition site added to the initiation codon site and an EcoRI recognition site added just behind the termination codon. The PCR was carried out using Pyrobest DNA Polymerase (product of Takara Bio Inc.) as a DNA polymerase and the reaction conditions were established according to the instruction manual attached thereto. This DNA was digested with NdeI and EcoRI and the resulting fragment was inserted into the plasmid pUCN18 (plasmid derived from pUC18 (product of Takara Bio Inc.) by substitution of A for the 185th T by PCR to destruct the relevant NdeI site and further substitution of TG for the 471st-472nd GC to newly introduce an NdeI site) between the NdeI recognition site and EcoRI recognition site downstream from the lac promoter to give a recombinant vector, PNBD. The descriptions "185th T" and "471st-472nd GC" as used herein are in accordance with the description in GenBank Accession No. L09136.

EXAMPLE 7

Construction of Expression Vector Further Containing Glucose Dehydrogenase Gene

Using primer 7: 5'-CAGGAGCTCTAAGGAGGTTAA-CAATGTATAAAG-3' (SEQ ID NO:10 in the sequence listing) and primer 8: 3'-CACGGATCCTTATCCGCGTCCT-GCTTGG-5' (SEQ ID NO:11 in the sequence listing) and using the plasmid pGDK1 (capable of being prepared by the method described in Eur. J. Biochem., 186, 389 (1989)) as the template, PCR was carried out. Then, there was obtained a double-stranded DNA containing: the *Escherichia coli* ribosome binding sequence added at a site 5 bases upstream of the initiation codon of the *Bacillus megaterium* IAM 1030 strain (available from the IAM culture collection (zip code 113-0032, 1-1-1 Yayoi, Bunkyo-ku, Tokyo Metropolis, Japan))-derived glucose dehydrogenase (hereinafter referred to as "GDH") gene; a SacI recognition site added just in front of that sequence; and a BamHI recognition site added jest behind the termination codon. The DNA fragment obtained was digested with SacI and BamHI and the resulting fragment was inserted into the plasmid PNBD at a site between the SacI recognition site and BamHI recognition site as occurring downstream from the lac promoter of the plasmid PNBD described in Example 6; a recombinant vector pNBDG was thus constructed. The process for construction and the structure of pNBDG are shown in FIG. 1.

EXAMPLE 8

Transformant Production

The recombinant vector pNBD constructed in Example 6 was used to transfect competent cells of *E. coli* HB101 (product of Takara Bio Inc.), and *E. coli* HB101 (pNBD) was obtained.

Similarly, the recombinant vector pNBDG constructed in Example 7 was used to transfect competent cells of *E. coli* HB101 (product of Takara Bio Inc.), and *E. coli* HB101 (pNBDG) was obtained.

EXAMPLE 9

Gene Expression in Transformant

Five milliliter of 2×YT medium (1.6% tryptone, 1.0% yeast extract, 0.5% NaCl, pH 7.0) containing 200 µg/ml ampicillin were respectively inoculated with the two transformants obtained in Example 8 and *E. coli* HB101 (pUCN18) (Comparative Example), which is a transformant harboring the vector plasmid pUCN18, followed by 24 hours of shake culture at 37° C. Cells were collected from each culture by centrifugation and suspended in 5 ml of 100 mM phosphate buffer (pH 6.5). The cells were disrupted using a model UH-50 ultrasonic homogenizer (product of SMT Co., Ltd.), and the cell debris was removed by centrifugation to give a cell-free extract. The ethyl N-Boc-2-amino-3-cyclohexyl-3-oxopropionate reducing activity and GDH activity of this cell-free extract were measured; they are shown in Table 4 in terms of specific activity.

TABLE 4

| Specific activities of cell-free extracts | | |
|---|---|---|
| strain | reductase activity (U/mg) | GDH activity (U/mg) |
| *E. coli* HB101(pUCN18) | N.D. | N.D. |
| *E. coli* HB101(pNBD) | 0.003 | N.D. |
| *E. coli* HB101(pNBDG) | 0.003 | 119 |

N.D.; not detectable

In both the two transformants obtained in Example 8, the expression of ethyl N-Boc-2-amino-3-cyclohexyl-3-oxopropionate reducing activity was observed, as shown in Table 4. In the transformant *E. coli* HB101 (pNBDG) harboring the GDH gene, the expression of GDH activity was also observed. The ethyl N-Boc-2-amino-3-cyclohexyl-3-oxopropionate reducing activity was measured by the method described in Example 4. As for the GDH activity, glucose (0.1 M), the coenzyme NAD (2 mM) and the crude enzyme solution were added to 1 M Tris hydrochloride buffer (pH 8.0), the reaction was allowed to proceed at 25° C. for 1 minute, and the GDH activity was calculated from the rate of increase in absorbance at the wavelength 340 nm. Under these reaction conditions, the enzyme activity reducing 1 µmol of NAD to NADH in 1 minute was defined as 1 unit.

EXAMPLE 10

Production of Ethyl (2R,3R)—N-Boc-2-amino-3-cyclohexyl-3-hydroxypropionate Using Transformant To 5 ml of the *E. coli* HB101 (pNBDG) culture fluid obtained by cultivation in the same manner as in Example 9 were added 25 mg of glucose, 1 mg of NAD and 10 mg of ethyl N-Boc-2-amino-3-cyclohexyl-3-oxopropionate, and the mixture was stirred at 30° C. for 40 hours. After the lapse of 8 hours and 28 hours from the start of the reaction, 1 mg of NAD was further added each time; the conversion at 40 hour after the start of the reaction was 97%.

After completion of the reaction, the reaction mixture was extracted with ethyl acetate, and the organic layer obtained was dried over anhydrous sodium sulfate. The sodium sulfate was removed by centrifugation, and the organic solvent was distilled off under reduced pressure to give ethyl (2R,3R)—N-Boc-2-amino-3-cyclohexyl-3-hydroxypropionate. The optical purity of this product was not lower than 99% ee, with the threo:erythro ratio being 1.5:98.5.

The quantitation of ethyl N-Boc-2-amino-3-cyclohexyl-3-hydroxypropionate and the determination of the threo/erythro ratio thereof were carried out by capillary gas chromatography (column: GLSciences InertCAP 5 (ID 0.25 mm×30 m), column temperature: 200° C., carrier gas: helium (70 kPa), detection: FID). The measurement of the optical purity of ethyl N-Boc-2-amino-3-cyclohexyl-3-hydroxypropionate was carried out by capillary gas chromatography (column: Tokyo Kasei Kogyo CHIRALDEX G-TA (ID 0.25 mm×20 m), column temperature: 120° C., carrier gas: helium (70 kPa), detection: FID) following treatment with trifluoroacetic anhydride.

EXAMPLE 11

Production of Ethyl (2R,3R)—N-Boc-2-amino-3-cyclohexyl-3-hydroxypropionate Using Transformant The procedure of Example 10 was followed in the same manner except that the transformant E. coli HB101 (pNT-CRG) (capable of being prepared by the method described in WO 01/040450) in which a DNA coding for a Candida magnoliae-derived polypeptide had been expressed was used as the transformant and that NADP was used in lieu of NAD. As a result, the conversion at 40 hour was 55% and the optical purity of the ethyl (2R,3R)—N-Boc-2-amino-3-cyclohexyl-3-hydroxypropionate obtained was not lower than 99% ee, with the threo:erythro ratio being 15:85.

EXAMPLE 12

Production of Ethyl 2S,3S)—N-Boc-2-amino-3-cyclohexyl-3-hydroxypropionate Using Transformant The procedure of Example 10 was followed in the same manner except that the transformant E. coli HB101 (pNTOM5G1) (capable of being prepared by the method described in WO 2006/013801) in which a DNA coding for a Pichia minuta var. minuta-derived polypeptide had been expressed was used as the transformant and that NADP was used in lieu of NAD. As a result, the conversion at 40 hour was 97% and the optical purity of the ethyl (2S,3S)—N-Boc-2-amino-3-cyclohexyl-3-hydroxypropionate obtained was not lower than 99% ee, with the threo:erythro ratio being 0:100.

EXAMPLE 13

Substrate Specificity of Polypeptide

Each carbonyl compound to serve as a substrate and the coenzyme NADH were dissolved, to respective final concentrations of 2 mM and 0.167 mM, in 100 mM phosphate buffer (pH6.5) containing 0.4% (v/v) of dimethyl sulfoxide. Thereto was added an appropriate amount of the purified polypeptide obtained in Example 4, and the reaction was allowed to proceed at 30° C. for 3 minutes. Based on the rate of decrease in the absorbance, at the wavelength 340 nm, of the reaction mixture, the reducing activity was calculated for each carbonyl compound and expressed in terms of relative value, with the activity against ethyl N-Boc-2-amino-3-cyclohexyl-3-oxopropionate being taken as 100%. The data thus obtained are shown in Table 5. As is evident from Table 5, the polypeptide as an embodiment of the present invention showed reducing activity against a broad range of carbonyl compounds.

TABLE 5

Levels of reducing activity against carbonyl compounds

| substrate | relative activity (%) |
|---|---|
| Ethyl N-Boc-2-amino-3-cyclohexyl-3-oxopropionate | 100 |
| Ethyl 2-chloroacetoacetate | 7264 |
| Ethyl 2-methylacetoacetate | 425 |
| Ethyl 2-chloro-3-oxo-3-phenylpropionate | 1139 |
| Ethyl 4-chloroacetoacetate | 533470 |
| Methyl acetoacetate | 1095 |
| Ethyl 2-oxocyclopentanecarboxylate | 199 |
| Methyl pyruvate | 5625 |
| Ethyl 2-oxopentanoate | 6046 |
| Ethyl benzoylformate | 12198 |
| 2-hexanone | 1540 |
| chloroacetone | 4655 |
| 3-chloro-hydroxyacetone | 484 |
| o-chloroacetophenone | 350 |
| m-chloroacetophenone | 4368 |
| p-chloroacetophenone | 534 |
| 2,3'-dichloroacetophenone | 12719 |
| 2-chloroacetophenone | 12789 |
| 2,2,2-trifluoroacetophenone | 42277 |
| 4-acetylpyridine | 1149 |
| 2-acetylfuran | 164 |
| tetrahydrothiophen-3-one | 156 |
| acetylacetone | 273 |
| diacetyl | 4830 |
| camphorquinone | 4737 |
| n-hexylaldehyde | 2160 |
| methylglyoxal | 248 |
| 2-phenylpropionaldehyde | 621 |
| o-chlorobenzaldehyde | 1219 |
| m-chlorobenzaldehyde | 2138 |
| p-chlorobenzaldehyde | 445 |

The invention claimed is:

1. A method of producing an optically active alcohol, said method comprising the step of allowing a polypeptide or a transformant to act on a carbonyl group-containing compound, wherein the polypeptide is defined below under (a), (b), or (c):
(a) a polypeptide comprising the amino acid sequence shown in the sequence listing under SEQ ID NO: 2;
(b) a polypeptide comprising an amino acid sequence derived from the amino acid sequence shown in the sequence listing under SEQ ID NO: 2 by substitution, insertion, deletion and/or addition of one or no more than 20 amino acids, said polypeptide having an activity of asymmetrically reducing N-Boc-2-amino-3-cyclohexyl-3-oxopropionic acid ester represented by the formula (1):

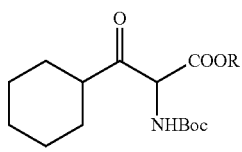

to form the corresponding (2R, 3R)—N-Boc-2-amino-3-cyclohexyl-3-hydroxypropionic acid ester represented by the formula (4):

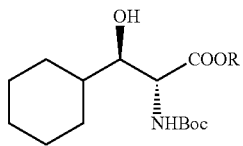

(wherein R is a substituted or unsubstituted alkyl group or aryl group);

(c) a polypeptide comprising an amino acid sequence showing 85% or higher sequence homology to the amino acid sequence shown in the sequence listing under SEQ ID NO: 2, said polypeptide having an activity of asymmetrically reducing the N-Boc-2-amino-3-cyclohexyl-3-oxopropionic acid ester represented by the formula (1) to form the corresponding (2R, 3R)—N-Boc-2-amino-3-cyclohexyl-3-hydroxypropionic acid ester represented by the formula (4), and wherein the transformant is obtained by transforming host cells with a vector comprising a DNA coding for the polypeptide, or a DNA defined below under (a), (b), or (c):
(a) a DNA comprising the base sequence shown in the sequence listing under SEQ ID NO: 1;
(b) a DNA capable of hybridizing with a DNA having a base sequence complementary to the base sequence shown in the sequence listing under SEQ ID NO: 1 under stringent conditions, said DNA coding for a polypeptide having an activity of asymmetrically reducing an N-Boc-2-amino-3-cyclohexyl-3-oxopropionic acid ester represented by the formula (1) to form the corresponding (2R, 3R)—N-Boc-2-amino-3-cyclohexyl-3-hydroxypropionic acid ester represented by the formula (4), wherein the stringent condition is the condition where hybridization is carried out in an aqueous solution comprising 75 mM trisodium citrate, 750 mM sodium chloride, 0.5% sodium dodecyl sulfate, 0.1% bovine serum albumin, 0.1% polyvinylpyrrolidone and 0.1% Ficoll 400 at 65° C., followed by washing with an aqueous solution containing 15 mM trisodium citrate, 150 mM sodium chloride and 0.1% sodium dodecyl sulfate at 65° C.;

(c) a DNA comprising a base sequence showing 85% or higher sequence homology to the base sequence shown in the sequence listing under SEQ ID NO: 1, said DNA coding for a polypeptide having an activity of asymmetrically reducing an N-Boc-2-amino-3-cyclohexyl-3-oxopropionic acid ester represented by the formula (1) to form the corresponding (2R, 3R)—N-Boc-2-amino-3-cyclohexyl-3-hydroxypropionic acid ester represented by the formula (4).

* * * * *